United States Patent
Langanki et al.

[11] Patent Number: 5,960,956
[45] Date of Patent: *Oct. 5, 1999

[54] STORAGE CONTAINER

[75] Inventors: Danney J. Langanki, Lino Lakes; Katherine S. Tweden, Mahtomedi, both of Minn.

[73] Assignee: St. Jude Medical, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/802,683

[22] Filed: Feb. 19, 1997

[51] Int. Cl.$^6$ .............................. A61B 17/06; B65D 85/30
[52] U.S. Cl. .......................... 206/440; 206/364; 206/5.1; 53/478
[58] Field of Search .................................. 206/204, 205, 206/210, 361, 363, 438, 5.1, 440, 364; 312/31; 53/409, 431, 471, 478

[56] References Cited

U.S. PATENT DOCUMENTS

| | | | |
|---|---|---|---|
| 980,127 | 12/1910 | Raabe | 312/31 |
| 1,987,373 | 1/1935 | Shapiro | 312/31 |
| 2,074,122 | 3/1937 | Harris | 312/31 |
| 2,740,683 | 4/1956 | June | 312/31 |
| 3,135,565 | 6/1964 | Bingham | 312/31 |
| 3,498,742 | 3/1970 | Long . | |
| 4,182,446 | 1/1980 | Penny | 206/205 |
| 4,211,325 | 7/1980 | Wright | 206/438 |
| 4,512,471 | 4/1985 | Kaster et al. . | |
| 4,597,765 | 7/1986 | Klatt . | |
| 4,736,850 | 4/1988 | Bowman et al. | 206/438 |
| 4,750,619 | 6/1988 | Cohen et al. . | |
| 4,824,788 | 4/1989 | Ferre . | |
| 4,965,074 | 10/1990 | Leeson | 424/449 |
| 5,069,904 | 12/1991 | Masterson | 424/449 |
| 5,135,715 | 8/1992 | Andersen . | |
| 5,560,487 | 10/1996 | Starr . | |
| 5,681,740 | 10/1997 | Messier et al. | 206/438 |

FOREIGN PATENT DOCUMENTS

| | | |
|---|---|---|
| 0 272 404 | 10/1987 | European Pat. Off. . |
| 2 665 173 | 7/1990 | France . |
| 92 00 371 U | 1/1992 | Germany . |
| 638 455 | 12/1978 | Switzerland . |
| 102103 | 4/1916 | United Kingdom . |

OTHER PUBLICATIONS

Seymour S. Block, Ph.D., *Disinfection, Sterilization, and Preservation,* Fourth Edition, Chapter 33, pp. 580–589, 1991 by Lea & Febiger.

Corkhill et al., "Synthetic Hydrogels—VI. Hydrogel Composites as Wound Dressings and Implant Materials", Biomaterials, vol. 10, pp. 3–10 (Jan. 1989).

Merrill et al., "Polyethylene Oxide as a Biomaterial", ASAIO Journal, vol. 6, pp. 60–64 (Apr./Jun. 1983).

*Primary Examiner*—Paul T. Sewell
*Assistant Examiner*—Luan K. Bui
*Attorney, Agent, or Firm*—Westman Champlin & Kelly, P.A.; Peter S. Dardi

[57] ABSTRACT

The invention involves containers and associated methods for the storage of devices in a moist environment without immersing the device in liquid. The containers have a moisture source that has a liquid supply isolated from a main chamber holding the device. The moisture source is in vapor communication with the main chamber to maintain a high relative humidity. The containers are conducive to storing the device in a sterile environment.

23 Claims, 1 Drawing Sheet

STORAGE CONTAINER

FIELD OF THE INVENTION

The invention relates to containers for the storage of devices, especially medical devices, in a moist environment.

BACKGROUND OF THE INVENTION

Devices produced using a variety of sensitive materials may have complicated storage requirements. Successful commercialization of devices incorporating sensitive materials requires consideration of any associated storage difficulties. In particular, composite materials may include a combination of materials, each having a different preferred environment for storage.

Certain sensitive materials require a moist environment because drying will irreversibly damage the material. Examples of materials that must be kept moist include biological tissues, as well as hydrogels, which are polymers with uses such as the production of soft contact lenses. Other materials may be sensitive to water or other liquids such that prolonged exposure to the liquid damages or degrades the material. Alternatively, liquid may commence degradation of the material prematurely, thereby shortening the shelf life of the product.

With respect to composite materials, storage considerations can be complicated by different moisture requirements for the different materials within the composite. For example, one component may be moisture requiring to prevent irreversible damage, and another component may be moisture sensitive, degrading gradually upon exposure to liquid. Furthermore, a liquid can leach components from one material that could be harmful to other materials.

Medical devices, in particular, can have stringent material requirements. Medical devices must perform with extremely high reliability, yet they generally must be capable of surviving harsh conditions used for sterilization. In addition, medical devices include products that may be extended or implanted into a patient's body, requiring the materials within these products to be compatible with the patient's bodily fluids.

SUMMARY OF THE INVENTION

Containers and associated methods of the invention provide for the storage of devices that have complex storage requirements. Specifically, the containers provide for the storage of devices that include materials that should be kept moist to maintain their integrity without immersing the devices in liquid, such as water. In this way, devices can be stored that include moisture sensitive material. The containers are particularly useful for the storage of composite materials, where materials within the composite have different storage requirements. The container provides for sterilization either by the inclusion of sterilants within the container or by subjecting the container to radiation.

In a first aspect, the invention involves a container including:
 a) a main chamber having an interior that is sealable from the ambient atmosphere; and
 b) a moisture source within the interior of the main chamber, the moisture source being in vapor communication with the main chamber, the moisture source having structure for storage of a supply of liquid in isolation from the main chamber.

In a preferred embodiment, the main chamber has a sealable lip near an opening into the interior of the main chamber, and the container further includes a cover that forms a seal with the lip of the main chamber. The moisture source can include a secondary chamber with passages that provide the vapor communication. The moisture source can include an absorbent material that permits the vaporization of liquid but generally can maintain the supply of liquid within itself. The main chamber can have an appropriate shape and size for the storage of an implantable prosthesis.

In another aspect, the invention involves a moist storage container including:
 a) a main chamber having an interior that is sealed from the ambient atmosphere;
 b) a moisture source in vapor communication with the interior of the main chamber, the moisture source comprising a supply of liquid in isolation from the interior of the main chamber; and
 c) a medical device within the interior of the main chamber.

The moist storage container preferably maintains the medical device in a sterile environment.

The medical device can include a moisture requiring material. The moisture requiring material can include a tissue and/or a hydrogel. The medical device can include a moisture sensitive material, possibly further including a liquid scavenger in contact with the moisture sensitive material. The moist storage container can further include a gas sterilant and/or a volatile sterilant within the interior of the main chamber. A volatile sterilant can be located within the moisture source.

In another aspect, the invention involves a method of storing a medical device in a moist environment including the step of sealing a medical device within a storage container, where the storage container includes:
 a) a main chamber having an interior sealable from the ambient atmosphere; and
 b) a moisture source in vapor communication with the interior of the main chamber, the moisture source comprising a supply of liquid isolated from the interior of the main chamber.

In the practice of the method, the storage container can include a chemical sterilant, such as a volatile liquid or a gas. The method of storing a medical device can further include the step of subjecting the storage container holding the medical device to radiation to produce a sterile environment for the medical device.

DESCRIPTION OF THE PREFERRED EMBODIMENTS

Figure 1:
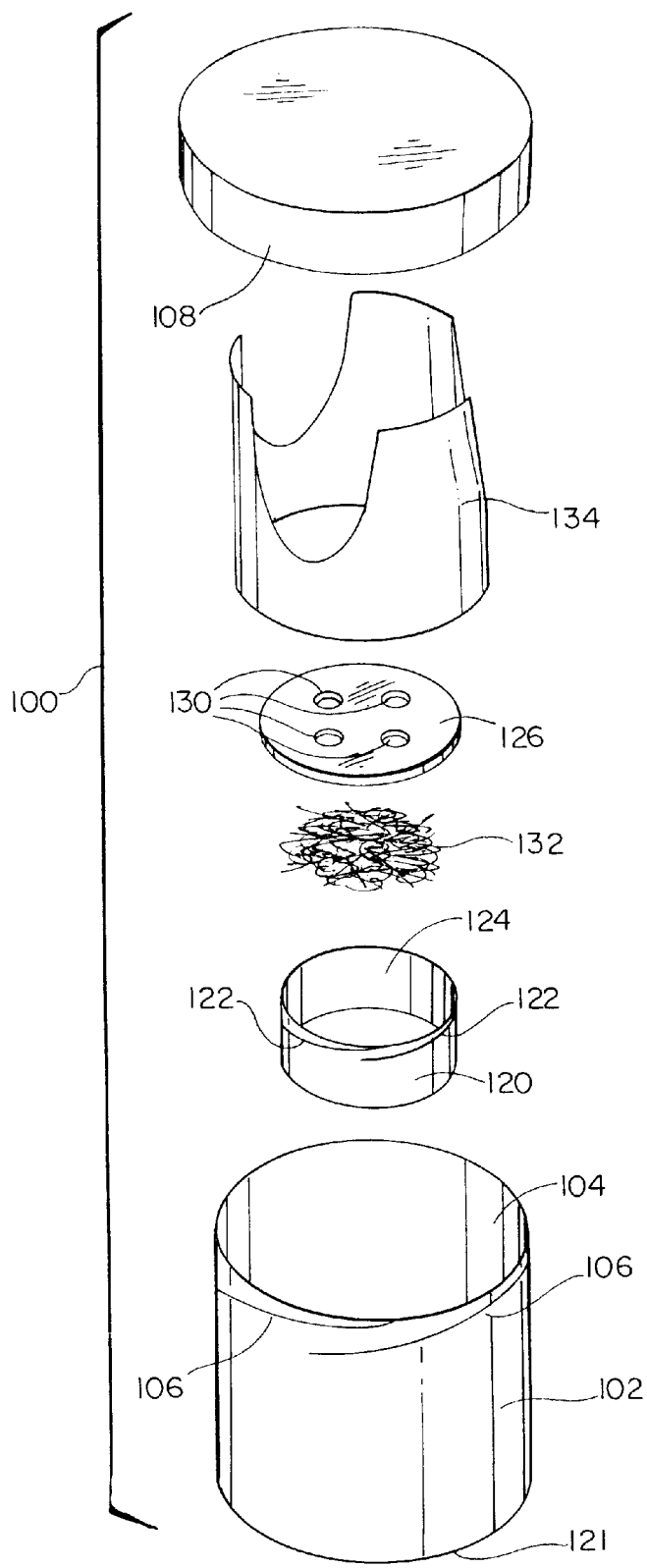
FIG. 1 is an expanded, perspective view of an embodiment of a storage container.

The invention provides for the storage of devices in a moist environment while reducing or eliminating the exposure of the device to liquid. While water is a preferred liquid and the focus of the discussion below, other volatile liquids, such as alcohols, formaldehyde, propylene oxide and beta-propiolactone, can be substituted for or combined with water to produce moisture vapor. To achieve the moist atmosphere, a container stores one or more devices in an environment isolated from the ambient atmosphere. A moisture source associated with the container provides sufficient vapor to keep the atmosphere in the isolated environment moist. The moisture source has a supply of liquid separated from the portion of the container holding the device.

This invention is especially useful for the storage of medical devices. The isolated environment preferably is sterile. The storage of a medical device without immersion in a liquid permits efficient sterilization using approaches that otherwise might not be effective, such as vapor phase sterilization.

Devices

Relevant containers are designed for the storage of any product that can be kept in a moist environment. The containers are especially useful where it is undesirable to subject the product to contact with significant quantities of liquid. In addition, the containers can be used for the storage of devices that must be sterile when removed from the containers. The containers can be sealed from the ambient atmosphere to prevent contamination by microbes.

Preferred devices include medical devices, particularly bioprostheses. Preferred medical devices can be kept in a moist environment to prevent irreversible degradation of the material. Thus, at least a portion of a preferred medical device generally is made from a moisture requiring material.

Medical devices with moisture requiring material generally are designed for contact with the bodily fluids of a patient. These articles can be organized roughly into three groups: implanted devices, percutaneous devices and cutaneous devices. Implanted devices broadly include articles that are fully implanted in a patient. Percutaneous devices include items that penetrate the skin, thereby extending from outside the body into the body. Cutaneous devices are used superficially, for example, at a wound site or at a moist membrane.

Implanted devices include, for example, prostheses such as transplant organs, artificial organs, heart valve prostheses, pericardial patches, vascular grafts, biological conduits, synthetic and bioprosthetic annuloplasty rings, bone, skin, ligaments and tendons. Preferred implanted devices include tissue heart valve bioprostheses. Percutaneous devices include, for example, catheters of various types. Catheters can be used for accessing various bodily systems such as the vascular system, the gastrointestinal tract, or the urinary system. Cutaneous devices include, for example, skin grafts, burn dressings, wound dressings of all types, and contact lenses.

Moisture sensitive materials include, for example, tissues and hydrogels. Tissues can include intact tissue as well as decellularized tissue. These tissues may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue. Appropriate tissues also include tissue equivalents such as a tissue-engineered material involving a cell-repopulated matrix, which can be formed from a polymer, biopolymers or from a decellularized natural tissue. Biopolymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment.

Tissues can be fixed by crosslinking. This provides mechanical stabilization, for example, by preventing enzymatic degradation of the tissue. Glutaraldehyde is typically used for fixation, but other fixatives can be used, such as epoxides and other difunctional aldehydes. Biological materials can be used in either crosslinked or uncrosslinked form, depending on the type of tissue, the use and other factors.

A variety of other surface modifications can be performed including incorporation of one or more of the following: growth factors, hydrogels, proteoglycans, cell adhesion molecules (CAMS), cytokines, chitosans, albumin, phospholipids, silk-like proteins, anticoagulants and bioadhesives. Growth factors include, for example, the fibroblast growth factors including acidic (1), basic (2) and FGF 3 through 9; platelet-derived growth factors including PDGF, PDGF-AA, PDGF-BB and PDGF-AB; transforming growth factors ($\beta 1-\beta 5$); epidermal growth factors including heparin binding EGF, transforming growth factor $\alpha$, and other members of the epidermal growth factor family; the insulin growth factors I and II; platelet-derived endothelial cell growth factors; and vascular endothelial growth factors. Some of these surface modifiers may be liquid sensitive.

Hydrogels can be produced from either natural or synthetic polymers. Natural polymers include, for example, dextran reduced with sodium borohydride and crosslinked with epichlorohydrin. Other natural polymers include, for example, keratin derivatives, glucoaminoglycans and collagen. Synthetic polymers for hydrogels include, for example, polyethylene oxide and block copolymers of hydroxyl terminated propylene and ethylene oxides. Other synthetic polymers include composites of poly acrylamide and polyurethane, poly vinyl alcohols and poly 2-hydroxyethyl methacrylate (HEMA). Hydrogels have been used in the production of burn dressings and implantable prostheses.

Hydrogels generally do not have a large degree of structural integrity. In many cases, hydrogels are applied as coatings or combined in other ways with other materials that provide added structural integrity. The hydrogel component generally is kept moist in order for the hydrogel to maintain its integrity as a coating.

Preferred devices also include devices incorporating liquid sensitive materials. Liquid sensitive materials include bioresorbable polymers, which degrade upon exposure to water. Other water sensitive materials can be made from certain polyesters, certain polyurethanes such as polyester polyurethane and low density calcium phosphates such as hydroxyapatite A liquid scavenger can be added to the liquid sensitive material to increase stability of the liquid sensitive material in a moist environment. For example, the liquid scavenger can be incorporated into pores within a bioresorbable polymer, into the polymer matrix during formation of the polymer structure or onto the surface of the bioresorbable material as a coating. Appropriate liquid scavengers include, for example, hydroscopic inorganic salts, dried or partially dried hydrogel polymers such as polyethylene glycol, alginate and proteoglycans such as hyaluronic acid.

Bioresorbable polymers include, for example, dextran, hydroxyethyl starch, gelatin, polyvinyl pyrolidone, polyvinyl alcohol, poly[N-(2-hydroxypropyl)methacrylamide], polyglycols, polyesters, poly orthoesters, poly esteramides, polyanhydrides and derivatives of gelatin. Preferred polyesters include, for example, poly (hydroxy acids) and copolymers thereof, poly (E-caprolactone), poly (dimethyl glycolic acid) and poly (hydroxy butyrate). Particular preferred poly (hydroxy acids) include polymers of D, L-polylactic acid, L-polylactic acid, polyglycolic acid and copolymers thereof, as described in U.S. Pat. No. 5,133,755. Other bioresorbable polymers include homopolymers and copolymers of recurring carbonate moieties as described in U.S. Pat. No. 5,412,068.

Container

The container of the invention generally will have a main chamber that can be sealed from the ambient atmosphere. The interior of the main chamber will hold the device for storage. The container includes a moisture source that provides moisture vapor to maintain the main chamber at a relatively high level of humidity. The moisture vapor source generally includes a supply of liquid, such as water, that is isolated from the device within the main chamber.

Specifically with respect to water, the amount of water needed to maintain the humidity will change with the temperature. Generally, it is preferred to keep the main chamber at about 100 percent relative humidity, although the container is also useful in applications where lower levels of relative humidity are acceptable. The humidity drops below 100 percent relative humidity if the amount of water in the supply is insufficient to maintain the saturated atmosphere at the particular temperature.

The size and shape of the main container generally are selected to provide a main chamber appropriate to hold a selected device or devices. Therefore, a container for a vascular prosthesis generally is relatively long and narrow. Similarly, a container for a heart valve prosthesis generally is cylindrical. The user can select the size and shape of the container as desired such that the main chamber is sufficiently large to hold the intended contents.

The manufacture of the container can be completed simultaneously with the storage of the device. In this case, the sealing of the container can be performed by forming the container around the device without any openings. The container then is opened by destroying the physical integrity of the container, typically at a predesigned weak location.

More preferably, the container is designed with the main chamber having an opening that can be sealed. The opening generally has a lip which interacts with a cover to form a seal. The lip and cover can encompass a wide variety of structures. In a preferred embodiment, the lip has a flat portion in the plane of the opening, and the cover is a piece of foil or other nonporous-air barrier material. The foil can be sealed by laminating the foil to the flat portion, for example with an adhesive. Similarly, induction sealing can be performed, where heat is used to facilitate adherence of a cover to the flat portion using an adhesive.

In another preferred embodiment, the lip is designed to engage a lid which snaps onto the lip. Alternatively, the lip includes threads. The cover is shaped like a cap and has threads mated with the threads of the lip. A container with this configuration is described in the Example below. An additional covering, such as a layer of parafilm or other polymer, can be added over the cover to ensure a proper seal from the ambient environment.

The container can be made from a variety of materials or combination of materials. Preferred materials include various polymers because of their low weight, moderate cost, high strength and chemical inertness. Preferred polymers include, for example, high density polyethylene and polypropylene. If a foil cover is used, the foil preferably is made from a polymer such as Tyvek™, metal or any other air barrier material.

The container includes a moisture source. The moisture source preferably is in vapor communication with the interior of the main chamber. In use, the moisture source includes a supply of liquid in isolation from the interior of the main chamber. The moisture source generally is smaller in volume than the main chamber. The moisture source may or may not include a secondary chamber.

The moisture source can be completely exterior to the main chamber, partly within the interior of the main chamber or completely within the interior of the main chamber. Preferably, the moisture vapor source is completely within the interior of the main chamber for ease of construction. If the moisture source is partly exterior to the main chamber or completely exterior to the main chamber, the main chamber must have a channel through its interior surface for passage of moisture vapor from the moisture source.

For example, the moisture source can be an absorbent material within the interior of the main chamber, where no secondary chamber is used. In this case, the liquid supply is contained within the absorbent material, and the liquid is isolated from the interior of the main chamber by the absorbent property of the material. If the moisture source includes a secondary chamber, the secondary chamber preferably is within the interior of the main chamber and preferably is attached to the interior surface of the main chamber.

The secondary chamber can be an appropriate size to hold sufficient liquid to maintain the humidity over the relevant temperature range. The necessary amount of liquid can be estimated easily using the vapor pressure of the liquid and the ideal gas equation. Excess liquid can be added to ensure 100 percent relative humidity at any reasonable temperature. Generally, the secondary chamber can have a volume considerably smaller than the main chamber, e.g., less than 10 percent of the volume of the main chamber.

The secondary chamber should be positioned so as not to interfere with storage of the device within the main chamber. The secondary chamber can be made from a variety of materials or combination of materials. Preferred materials include, for example, polymers, such as polypropylene.

The secondary chamber of the moisture source includes passages or pores that permit the transmission of water vapor from the interior of the secondary chamber to the interior of the main chamber. The passages can be formed, for example, by sections of a polymer sheeting, such as polytetrafluoroethylene, which permits the transmission of water vapor but resists the transmission of liquid water. Alternatively, the passages can be holes, slits or other openings through any part of the secondary chamber.

If the passages are openings, the moisture source preferably also includes an absorbent material within the secondary chamber. The absorbent material helps to prevent liquid from flowing from the secondary chamber if the container is subjected to jarring or inversion. Any absorbent material can be used such as, for example, gauze, hydrogels and natural or artificial sponges. The supply of liquid can be completely contained within the absorbent material.

Figure 2A:
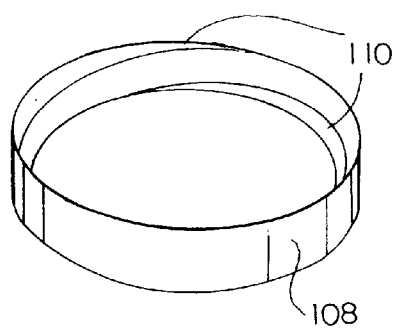
FIG. 2A is a perspective view of an inverted lid of the container of FIG. 1.
Figure 2B:
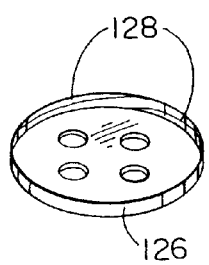
FIG. 2B is a perspective view of an inverted inner lid of the container of FIG. 1.

A particular embodiment of the container is depicted schematically in FIGS. 1 and 2. The container 100 has a main chamber 102, which is generally cylindrical. Main chamber 102 is made from high density polyethylene or other similar material and has a volume of about 45 mls. Along the outer surface near the opening into the interior 104, main chamber 102 has threads 106. Lid 108 has mated threads 110 such that lid 108 can be tightened onto main chamber 102 to seal interior 104, as shown in FIG. 2A. Lid 108 is made from polypropylene or other appropriate materials.

An inner chamber 120 preferably is attached, such as by an adhesive, to the bottom surface 121 of the interior 104 of main chamber 102. Inner chamber 120 may be a 1.2 ml cryogenic vial made from polypropylene or other appropriate materials. Inner chamber 120 has threads 122 near the opening to the interior 124 of inner chamber 120. Inner lid 126 has threads 128 mated with the threads 122 of inner chamber 120 such that the inner lid 126 can be tightened over the opening of inner chamber 120. A plurality of holes 130 are placed in inner lid 126. A piece of cellulose sponge 132 is located in the interior 124 of inner chamber 120. A device 134 can be placed in main chamber 102.

Use of the Container

The medical device can be placed within the container before or after introduction of liquid into the moisture source. Following placement of the desired amount of liquid and the intended device, the container is sealed to provide for establishment of the moist environment.

Many medical devices must be sterile when removed from the container for use. Preferably, both the medical device and the container are sterile prior to the placement of the medical device into the container. Furthermore, one or more sterilants can be placed within the container prior to the sealing of the lid.

For example, a volatile liquid can be placed within the main chamber. More preferably, a volatile liquid sterilant is used to form an aqueous solution within the moisture source. In this latter embodiment, the moisture source is a source of sterilizing vapor as well as water vapor. Examples of appropriate volatile liquids include formaldehyde, peracetic acid, hydrogen peroxide and propylene oxide, which are effective in a humid, water environment. The concentration of the sterilant in the aqueous solution can range from about 0.0001 grams to about 35 grams per 100 mls solution and more preferably from about 0.1 grams to about 26 grams per 100 mls of solution, depending on the sterilant.

Alternatively, a gas sterilant can be added to the container. Appropriate gas sterilants include, for example, ethylene oxide, beta propiolactone, chlorine dioxide and ozone. This can be done by sealing the lid while the container is under an atmosphere of the gas sterilant. Rather than placing a chemical sterilant into the container before sealing, if a deformable lid is used, a needle can be used to inject a volatile liquid or gas sterilant into the container without exposing the inside of the container to the ambient atmosphere.

As an alternative to chemical sterilants, radiation can be used to sterilize the container and the device within the container. Generally, radiation is applied after the device is sealed within the container. For example, a microwave, x-ray or gamma ray source can be used to sterilize the container and device. Alternatively, an electron beam can be used for sterilization. Electrons are less penetrating than microwaves, x-rays and gamma rays, so sterilization by electron beam is considerably more effective if the device is not immersed in water or other liquid, as described herein with respect to the present container. Electron beam sterilization can be used advantageously.

Heat may also be used for sterilization, but heat is less desirable than other approaches. Heat is not preferred because large temperature fluctuations tend to result in condensation of liquid on the device stored within the main chamber. The temperature variation needed to pasteurize the container and enclosed device generally would be larger than temperature variations otherwise encountered.

Following sterilization, medical devices are ready for distribution. Generally, the devices are shipped in the sealed containers to the end user. The containers preferably are not opened until the device is ready for use, for example, by a physician ready to implant a bioprosthetic device. Rinsing with sterile saline may be needed to remove traces of sterilant or other compounds.

Other volatile or gaseous preservatives can be added, if desired, for medical or nonmedical devices.

Containers described above have a number of advantages. The containers help prevent or retard degradation of moisture sensitive materials such as bioresorbable materials that are stored within the container. Since large volumes of liquid are not used, leakage of the containers is less likely. Also, partially soluble components of the devices such as growth factors and anticalcification agents are not washed out of the devices.

EXAMPLE

This example demonstrates the storage of a composite material including both a water requiring material (tissue) and a water sensitive material (bioresorbable polymer). Containers used in the example were manufactured as described above with respect to the schematic representation in FIGS. 1 and 2. These containers had an inner chamber attached with cyanoacrylate polymer to the bottom of the main chamber. Also, the inner lid had four 3/16 inch holes.

Six tissue samples were prepared using 3 cm×2 cm pieces of root tissue from a porcine heart valve and 3 cm×2 cm pieces of bioresorbable, polylactic acid (PLA), St. Jude Medical Prototype #9 obtained from THM Biomedical, Inc., Duluth, Minn. On a bench top, PLA samples were attached to the tissue samples using a whip suture along the perimeter to form tight PLA/tissue constructs. The PLA samples had been plasma gas sterilized. The tissue samples had been sterilized by exposure to glutaraldehyde.

Two containers, including the chambers and lids, were sterilized by steam. Three PLA/tissue samples were placed vertically in each container. In a sterile hood, each inner chamber was packed half full with sterile gauze, and 0.75 ml sterile water was added. The inner lids were secured, and the lids were tightened on the containers. The seal of the lids were assured by wrapping the interface of the lid and the main chamber with parafilm.

The samples were stored on a bench top for just over 7 months. Following seven months the containers were opened and the samples examined. Small amounts of moisture had condensed onto the samples during the seven month period.

The tissue had normal color, elasticity and texture following the storage period. Collagen integrity was measured by Differential Scanning Calorimetry measurements, to determine the shrink temperature. The shrink temperatures for a tissue sample from each container were 88.0° C. and 91.1° C. The shrink temperature for a control that had been stored using typical tissue storage conditions (0.5 percent buffered glutaraldehyde covering the tissue) was 86.2° C. The measurements demonstrate that no significant denaturing occurred following seven months of incubation in the high moisture environment. The PLA showed some signs of degradation, although the material had greater physical integrity than comparable material would have following even a short time immersed in water.

Other embodiments of the invention are within the claims below.

What is claimed is:

1. A moist storage container comprising:
   a) a main chamber having an interior that is sealed from the ambient atmosphere;
   b) a moisture source in vapor communication with said interior of said main chamber, said moisture source comprising a supply of liquid in isolation from said interior of said main chamber; and c) a medical device within said interior of said main chamber, said medical device being isolated from said supply of liquid, and said medical device being selected from the group consisting of prostheses, catheters, skin grafts, burn dressings, wound dressings and contact lenses.

2. The container of claim 1, wherein said main chamber has a sealable lip near an opening into said interior of said main chamber and said container further comprises a cover that forms a seal with said lip of said main chamber.

3. The container of claim 1, wherein said moisture source comprises a secondary chamber with passages that provide said vapor communication and further comprises an absorbent material that permits the vaporization of liquid but generally can maintain said supply of liquid within itself.

4. The moist storage container of claim 1, wherein said medical device is kept in a sterile environment.

5. The moist storage container of claim 1, further comprising a gas sterilant within said interior of said main chamber.

6. The moist storage container of claim 1, further comprising a volatile sterilant.

7. The moist storage container of claim 6, where said volatile sterilant is located within said moisture source.

8. The moist storage container of claim 1, wherein said medical device comprises a moisture requiring material.

9. The moist storage container of claim 8, wherein said moisture requiring material comprises a tissue.

10. The moist storage container of claim 8, wherein said moisture requiring material comprises a hydrogel.

11. The moisture storage container of claim 1, wherein said medical device comprises a moisture sensitive material.

12. The moisture storage container of claim 11, wherein said medical device comprises a liquid scavenger in contact with said moisture sensitive material.

13. The moist storage container of claim 1, wherein the medical device comprises a heart valve prosthesis.

14. The moist storage container of claim 1 wherein the medical device comprises a prosthesis.

15. A method of storing a medical device in a moist environment within a storage container, where said storage container comprises:

a) a main chamber having an interior sealable from the ambient atmosphere, said medical device being within said interior of said main chamber;

b) a moisture source in vapor communication with said interior of said main chamber, said moisture source comprising a supply of liquid isolated from said interior of said main chamber and from said medical device, the method comprising sealing said medical device in the interior volume of said main chamber, and said medical device being selected from the group consisting of prostheses, catheters, skin grafts, burn dressings, wound dressings and contact lenses.

16. The method of claim 15, wherein said medical device comprises tissue.

17. The method of claim 15, wherein said storage container comprises a chemical sterilant.

18. The method of claim 17, wherein said chemical sterilant is a volatile liquid.

19. The method of claim 17, wherein said chemical sterilant is a gas.

20. The method of claim 15, further comprising the step of subjecting said storage container holding said medical device to radiation to produce a sterile environment for said medical device.

21. The method of claim 15 wherein the medical device comprises a heart valve prosthesis.

22. The method of claim 15 wherein the medical device comprises a prosthesis.

23. A storage container comprising:

a) a main chamber having an interior that is sealed from the ambient atmosphere;

b) a moisture source in vapor communication with said interior of said main chamber, said moisture source comprising a supply of liquid in isolation from said interior of said main chamber; and c) a medical device within said interior of said main chamber, said medical device being isolated from said supply of liquid and said medical device being in a sterile environment.

* * * * *